(12) United States Patent
Tanimoto

(10) Patent No.: US 9,086,225 B2
(45) Date of Patent: Jul. 21, 2015

(54) ISOLATOR SYSTEM

(71) Applicant: SHIBUYA KOGYO CO., LTD., Ishikawa (JP)

(72) Inventor: Kazuhito Tanimoto, Ishikawa (JP)

(73) Assignee: SHIBUYA KOGYO CO., LTD., Ishikawa (JP)

( * ) Notice: Subject to any disclaimer, the term of this patent is extended or adjusted under 35 U.S.C. 154(b) by 0 days.

(21) Appl. No.: 14/224,583

(22) Filed: Mar. 25, 2014

(65) Prior Publication Data

US 2014/0290162 A1 Oct. 2, 2014

(30) Foreign Application Priority Data

Mar. 29, 2013 (JP) .................................. 2013-073950

(51) Int. Cl.
| | |
|---|---|
| *F24F 3/16* | (2006.01) |
| *A61G 10/02* | (2006.01) |
| *C12M 1/12* | (2006.01) |
| *B25J 21/02* | (2006.01) |
| *A61G 10/00* | (2006.01) |

(52) U.S. Cl.
CPC .................. *F24F 3/161* (2013.01); *B25J 21/02* (2013.01); *C12M 37/00* (2013.01); *A61G 10/005* (2013.01)

(58) Field of Classification Search
CPC ....... F24F 3/161; F24F 3/1607; F24F 3/1603; F24F 2011/0005; A61L 2/24; A61L 2/022; A61L 2202/122
USPC ....... 52/169.6, 79.1, 79.7, 79.8; 109/1 S, 1 V, 109/58, 62, 63; 128/846, 847, 849, 853, 128/854; 454/187, 188, 189
See application file for complete search history.

(56) References Cited

U.S. PATENT DOCUMENTS

| | | | | |
|---|---|---|---|---|
| 3,505,989 A | * | 4/1970 | Truhan | ............................ 600/21 |
| 3,601,031 A | * | 8/1971 | Abel et al. | ..................... 454/187 |
| 3,875,853 A | * | 4/1975 | Pielkenrood | ................... 454/187 |
| 4,804,392 A | * | 2/1989 | Spengler | ......................... 55/356 |
| 5,314,377 A | * | 5/1994 | Pelosi, III | ...................... 454/187 |
| 5,316,541 A | * | 5/1994 | Fischer | ............................ 600/21 |
| 5,645,480 A | * | 7/1997 | Spengler | ....................... 454/187 |
| 5,997,399 A | * | 12/1999 | Szatmary | ....................... 454/187 |
| 6,010,400 A | * | 1/2000 | Krainiak et al. | ............... 454/187 |
| 7,156,897 B2 | * | 1/2007 | Wen | .................................. 95/28 |

(Continued)

FOREIGN PATENT DOCUMENTS

| | | |
|---|---|---|
| JP | 2012-044964 A | 3/2012 |
| JP | 4924570 B2 | 4/2012 |

*Primary Examiner* — Elizabeth A Plummer
*Assistant Examiner* — Kyle Walraed-Sullivan
(74) *Attorney, Agent, or Firm* — Greenblum & Bernstein P.L.C.

(57) ABSTRACT

An isolator system includes an isolator, passbox, clean booth, and decontamination gas supply. The isolator includes a sterile operation area and a wearing entity for an operator. The passbox enables introducing an object into the sterile operation area. The clean booth, encloses an insertion port of the wearing entity and an inlet port for introducing the object into the passbox. A clean gas supply supplies clean gas to the sterile operation area and to the clean booth. The decontamination gas supply supplies decontamination gas into the sterile operation area and the clean booth. After an interior of the sterile operation area and the clean booth are decontaminated, pressures of the sterile operation area and the clean booth are maintained at least equal to a building pressure and the pressure of the clean booth is maintained lower than a pressure of the sterile operation area.

5 Claims, 4 Drawing Sheets

(56) References Cited

U.S. PATENT DOCUMENTS

| | | | |
|---|---|---|---|
| 7,323,025 B2* | 1/2008 | Weidner | 55/385.2 |
| 7,393,373 B1* | 7/2008 | Krippner et al. | 55/385.2 |
| 7,465,225 B2* | 12/2008 | Ohmura et al. | 454/187 |
| 8,012,228 B2* | 9/2011 | Polsky | 55/385.2 |
| 8,034,141 B2* | 10/2011 | Polsky | 55/385.2 |
| 2006/0003685 A1* | 1/2006 | Rothbauer et al. | 454/187 |
| 2009/0017747 A1* | 1/2009 | Wu et al. | 454/189 |
| 2010/0105309 A1* | 4/2010 | Ishibashi | 454/187 |
| 2010/0189607 A1* | 7/2010 | Yokoi et al. | 422/116 |
| 2013/0252533 A1* | 9/2013 | Mauck et al. | 454/187 |

\* cited by examiner

ISOLATOR SYSTEM

BACKGROUND OF THE INVENTION

1. Field of the Invention

The present invention relates to an isolator system including an isolator, in which a sterile operation area is arranged, and a pass box for introducing an object into the sterile operation area.

2. Description of the Related Art

Currently, a culture of human cells and tissues, and the operation and research thereof are performed in a facility called a cell processing center (CPC). In such a facility, the interior of a building is divided into a plurality of rooms and these rooms are arranged so that cleanliness thereof is enhanced stepwise. A space in which a cell vessel is opened is an important operation region required to have the highest cleanliness environment of grade A. An ambient environment thereof, which is a direct support region, is required to be grade B with the second highest cleanliness. Further, a two-step improvement of cleanliness is required to go from a general environment of grade D through grade C to reach the grade B cleanliness level of the direct support region (for example, see "Regeneration Medicine Field (Design guideline for human cell culture device (revised)", Development Guideline 2009, Ministry of Economy, Trade and Industry, 2010, February).

Under present circumstances, when conducting regenerative medical research using cell cultures as described above, the preparation of facilities including a building is required, causing substantial facility investment and maintenance costs. Here, in a case of adopting an isolator that can ensure sterility, the inside of a sterile operation area can be maintain at a grade A cleanliness level even if an ambient environment thereof is grade D as long as a pass box having a decontamination function is equipped for transporting an object to and from the inside of the sterile operation area. Further, even in a case of using a pass box without a decontamination capabilities, it is possible to use the inside of the sterile operation area as a grade A environment by setting the environment of the pass box to grade B while sequentially enhancing a general environment to grade D and grade C.

There is known an isolator system that includes a pass box having a decontamination function and an isolator system that includes a pass box without a decontamination function (for example, see Japanese Patent No. 4924570 or Japanese Unexamined Patent Publication No. 2012-44964).

An isolator system according to an invention disclosed in Japanese Patent No. 4924570 includes an isolator compartment having the inside thereof maintained in a sterile condition, a pass box for transporting an object to and from the isolator compartment that is connected to the isolator compartment, and a decontamination gas supply unit which supplies decontamination gas into the isolator compartment and the pass box.

A sterile operation device according to an invention disclosed in Japanese Unexamined Patent Publication No. 2012-44964 includes a hydrogen peroxide vapor supply unit which supplies hydrogen peroxide vapor into an operation area isolated from an external environment and decontaminates the inside of the operation area.

SUMMARY OF THE INVENTION

An object of the present invention is to maintain a culture of human cells and tissues, and the operation and research thereof without a specially organized facility such as a cell processing center.

According to the present invention, an isolator system includes an isolator in which a sterile operation area is arranged and which includes a wearing entity for an operator to operate externally; a pass box for transporting an object into the sterile operation area; a clean booth in which an operator can enter, which encloses at least an external insertion port of the wearing entity arranged at the isolator and an object inlet port through which the object is placed into the pass box, and which includes a clean gas supply unit to supply clean air to an internal space thereof; and a decontamination gas supply unit which supplies decontamination gas to the sterile operation area and the clean booth. The isolator, the pass box, and the clean booth are arranged in the building, and the internal air pressure of the clean booth is maintained equal to or higher than the ambient air pressure in the building, but lower than the air pressure of the sterile operation area after the interiors of the sterile operation area and the clean booth have been decontaminated with the decontamination gas.

Here, the isolator, the pass box, and the clean booth are arranged in the building. After the interiors of the sterile operation area in the isolator and the clean booth are decontaminated, the air pressure of the clean booth is maintained higher than the ambient air pressure in the building but lower than the air pressure of the sterile operation area. According to the above, the invention disclosed herein provides the advantage of being able to research and process cultures of human cells and tissues without a specially organized facility such as a cell processing center.

BRIEF DESCRIPTION OF THE DRAWINGS

The object and advantages of the present invention will be better understood from the following description, with reference to the accompanying drawings in which.

DESCRIPTION OF THE PREFERRED EMBODIMENTS

Figure 1:
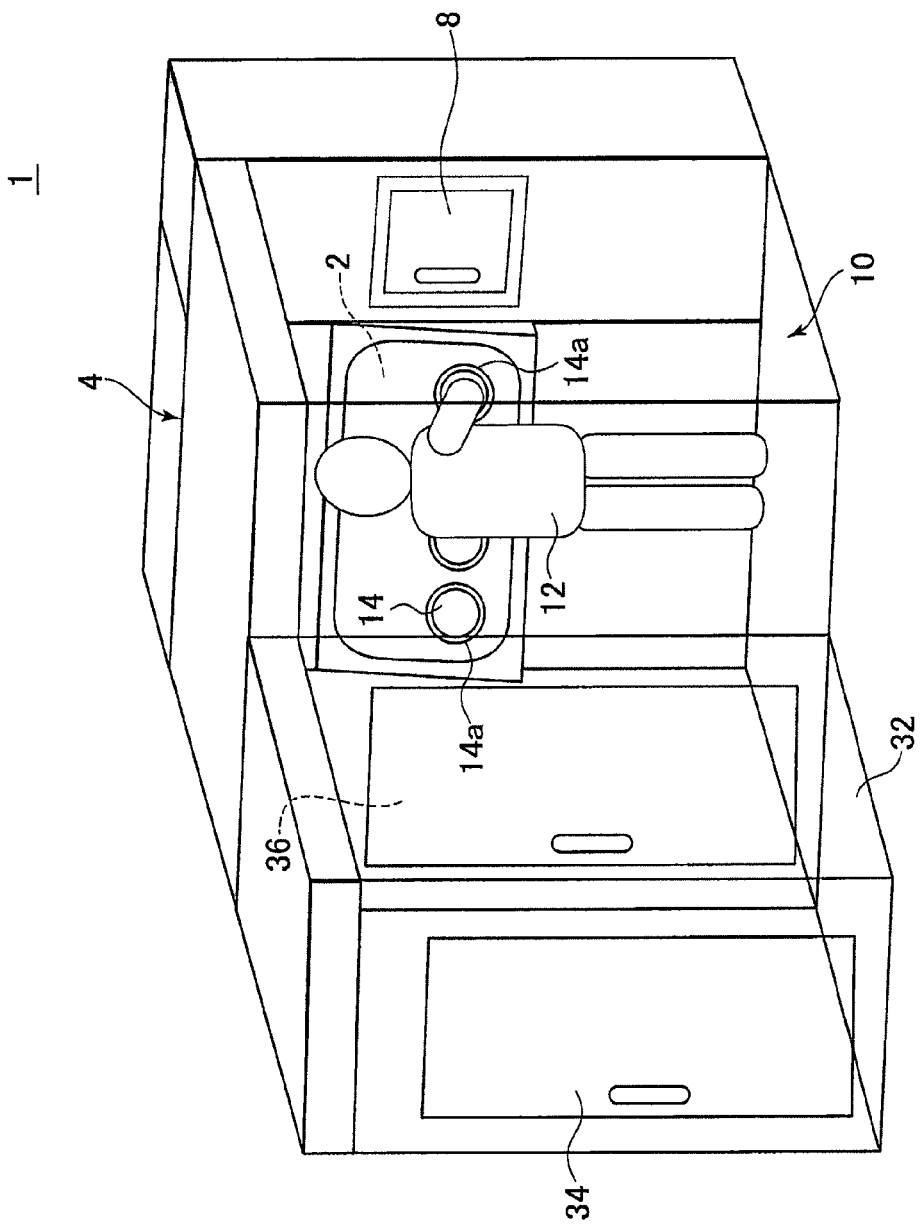
FIG. 1 is a perspective view of an isolator system according to a first embodiment of the present invention.

In the following, the present invention will be described with a first embodiment which is illustrated in the drawings. An isolator system 1 includes an isolator compartment (isolator) 4 with a sterile operation area 2 formed therein, and a pass box 8 through which an object 6 (in the present embodiment, a culture vessel for human cells and tissues, or the like) is inserted and removed from the operation area 2. The isolator system 1 allows an operator 12 to enter thereinto. Further, as described later, the isolator system 1 includes a clean booth 10 which encloses a section from which an operator can work with the object in the isolator compartment 4 and a section through which objects can be placed into the pass box 8.

The sterile operation area 2 capable of maintaining a grade A cleanliness environment A is formed inside the isolator compartment 4. A glove 14 is arranged as a wearing entity with which the operator 12 positioned outside of the isolator compartment 4 processes the object 6 placed in the sterile operation area 2. Here, in addition to the glove 14 in which only an arm of the operator 12 is inserted, it is also possible to arrange a coat as a wearing entity that covers the upper body of the operator.

An opening portion 16a through which the object 6 is inserted and removed is arranged in a side wall 16 of the isolator compartment 4. An inlet pass box 8 is connected to the outside of the opening portion 16a. An internal door 18 which provides and blocks access between the inside of the isolator compartment 4 and the inside of the inlet pass box 8 when opened and closed, respectively, is arranged in the opening portion 16a. The internal door 18 opens toward the inside of the isolator compartment 4. An object inlet port 20a through which the object 6 is introduced into the inlet pass box 8 from the outside is arranged in a side wall 20 that is different from the side wall of the inlet pass box 8 adjoining the isolator compartment 4. An external door 22 which opens and closes the object inlet port 20a is arranged therein. The external door 22 opens toward the outside of the inlet pass box 8.

Figure 2:
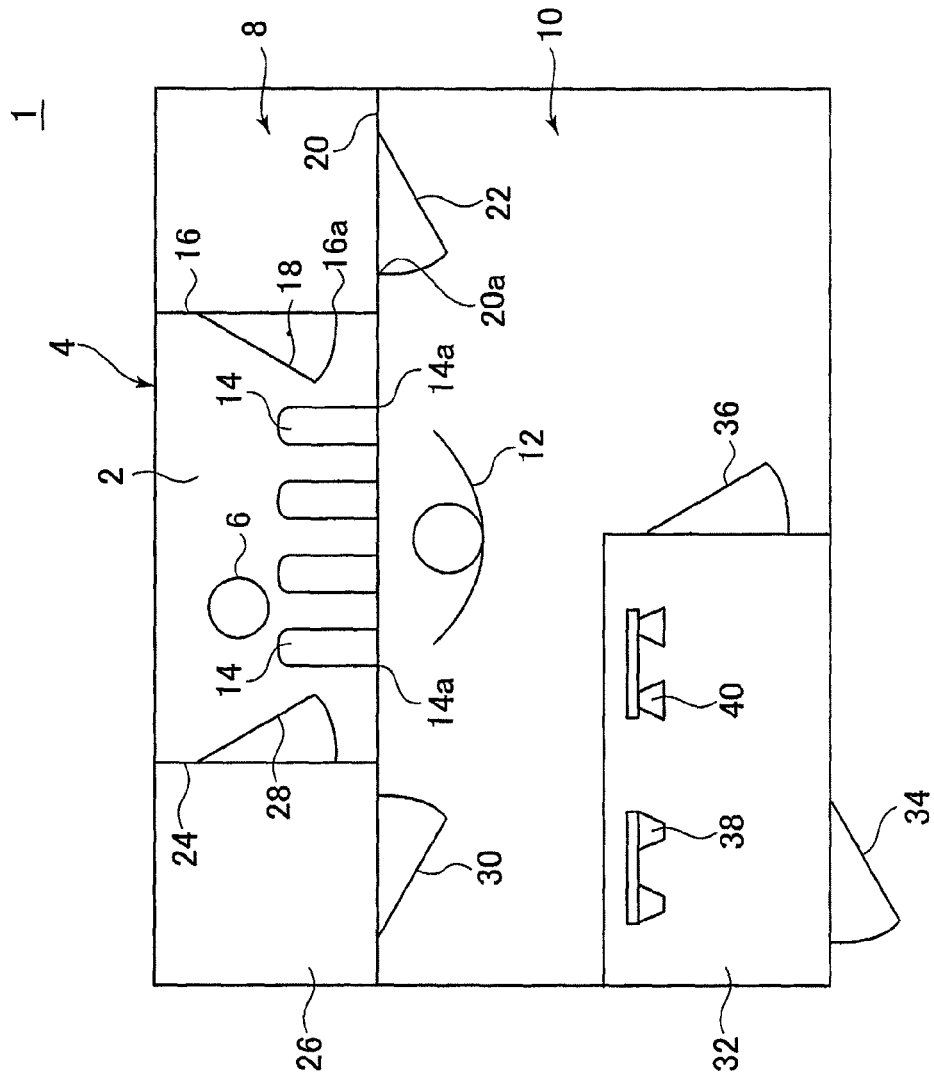
FIG. 2 is a plan view of the isolator system.

An outlet pass box 26 is connected to a side wall 24 of the isolator compartment 4 (a left side wall in FIG. 2) opposite to the side wall 16 to which the inlet pass box 8 is connected (see FIG. 2). Similarly to the inlet pass box 8, the outlet pass box 26 is provided with an internal door 28 which opens toward the inside of the isolator compartment 4 and an external door 30 which opens toward the outside of the outlet pass box 26.

The clean booth 10 is simply required to maintain a grade D environment by maintaining a higher interior air pressure than the ambient pressure in a building. Therefore, by adopting a simple structure in which walls are arranged with an acrylic plate or a plastic sheet on a steel or aluminum frame, the clean booth 10 can be easily arranged in a room. Since a plastic sheet cannot be provided with a door, the arrangement of a fastener or an overlapping portion enables it to be opened and closed. Further, in a case with a soft material such as a plastic sheet, it is also possible to be set up like a curtain and attached to a rail arranged on a ceiling. The clean booth 10 encloses at least an external insertion port 14a of the glove 14 provided in the isolator compartment 4, the object inlet port 20a with the external door 22 through which the object 6 is introduced into the inlet pass box 8 and an object outlet port through which the object 6 is removed from the outlet pass box 26. The clean booth 10 allows the operator 12 to enter thereinto.

An air lock room 32 is arranged at an entrance side of the clean booth 10, which is configured to enclose operation portions of the isolator compartment 4, the inlet pass box 8, and the outlet pass box 26. The air lock room 32 blocks communication between the inside of the clean booth 10 and general external environment (room inside of a building in which the isolator system 1 is installed). The air lock room 32 is provided with an entrance door 34 and an exit door 36. Inflow of external air into the clean booth 10 from the outside thereof can be prevented by closing one of the doors 34, 36 while the other door remains opens. A sterile air nozzle 38, which is a dust remover, and an alcohol injection nozzle 40, which is a sterilizer, are arranged inside of the air lock room 32. The operator 12 entering the clean booth 10 from the outside and the object 6 being carried in from the outside are first processed by the sterile air nozzle 38 blowing air to remove dust brought in from the outside, and further, completely sterilized by the alcohol injection nozzle 40. Then, the operator 12 enters or the object 6 is carried into the clean booth 10.

Figure 3:
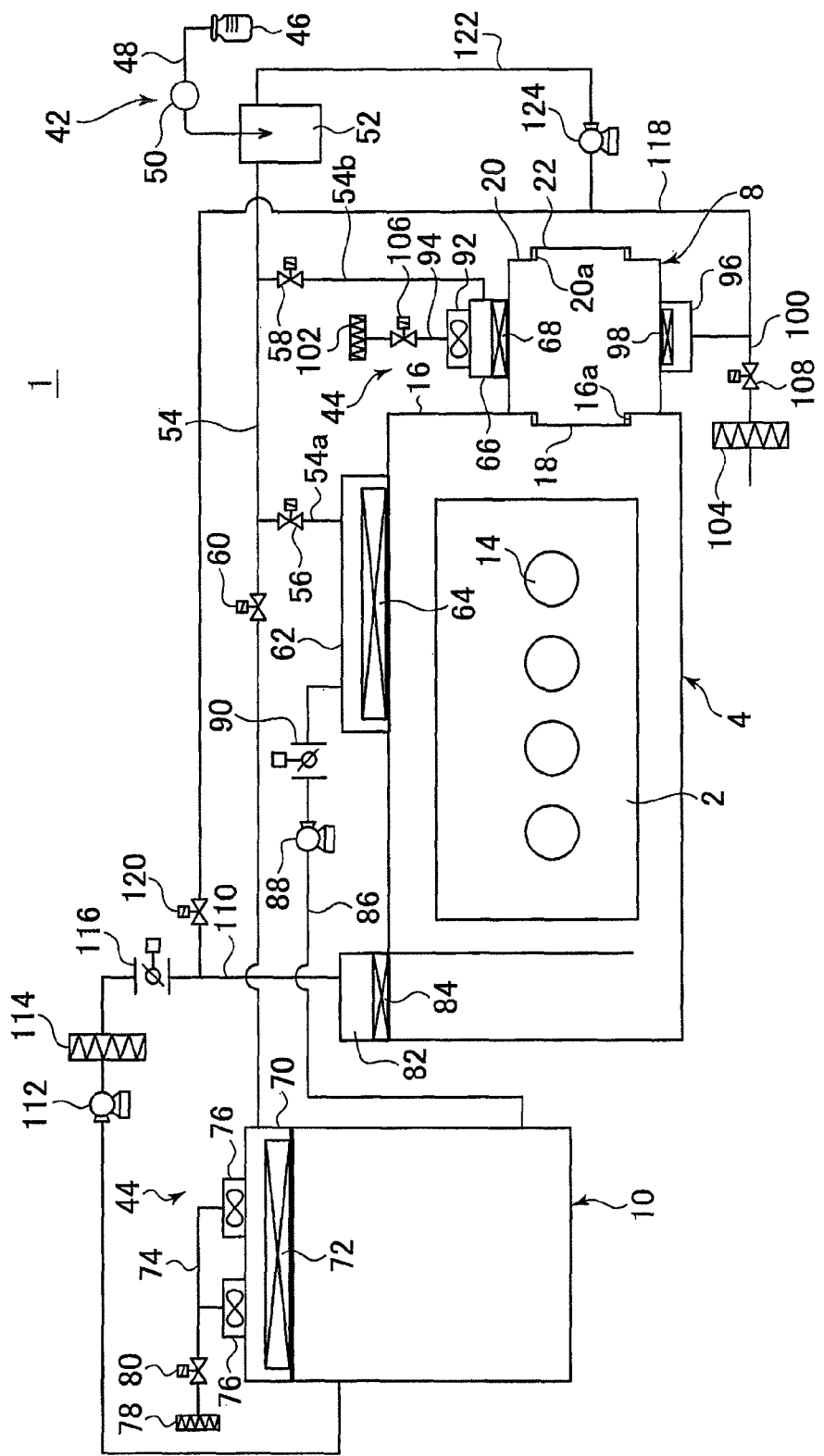
FIG. 3 is a circuit diagram of a clean gas supply unit and a decontamination gas supply unit which are arranged in the isolator system.
Figure 4:
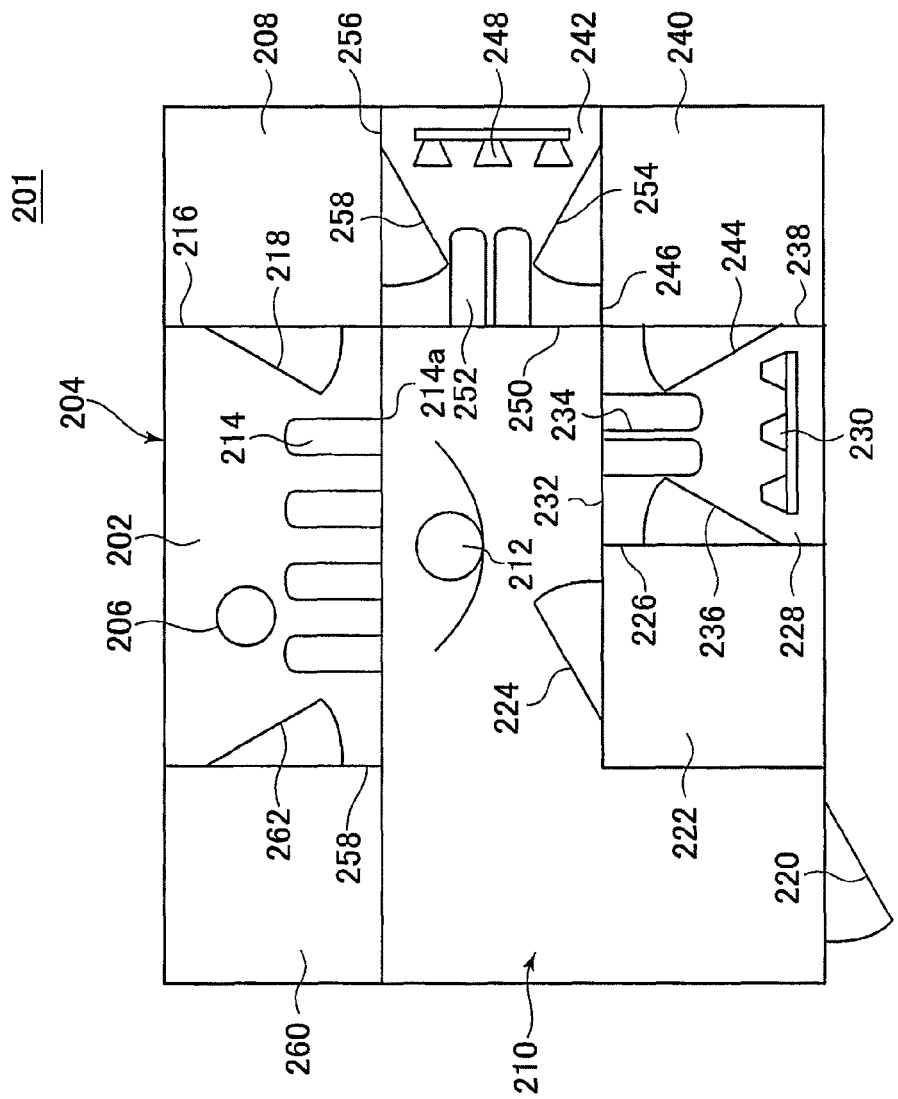
FIG. 4 is a plan view of an isolator system according to a second embodiment.

Next, a description will be provided with reference to FIG. 3 for a decontamination gas supply unit 42 which supplies decontamination gas to the interiors of the isolator compartment 4, the inlet pass box 8, and the clean booth 10, and for a clean gas supply unit 44 which supplies clean gas to those same interiors. Here, the outlet pass box 26 and the air lock room 32 are not illustrated in FIG. 3. However, the decontamination gas and the clean gas are supplied to and discharged from the outlet pass box 26 by a similar circuit as in the case for the inlet pass box 8, and supplied to and discharged from the air lock room 32 by a similar circuit as in the case for the clean booth 10. Accordingly, a description thereof will be omitted. The decontamination gas supply unit 42 and the clean gas supply unit 44 are configured with the isolator system integrated with the isolator compartment 4.

The decontamination gas supply unit 42, which supplies decontamination gas in the sterile operation area 2 in the isolator compartment 4, the inlet pass box 8 (the outlet pass box 26), and the clean booth 10 (the air lock room 32), is provided with a tank 46 that stores a decontamination agent such as aqueous hydrogen peroxide. The aqueous hydrogen peroxide is supplied by a constant amount from the tank 46 to an evaporator 52 by a pump 50 which is arranged in a decontamination agent supply path 48. The aqueous hydrogen peroxide supplied to the evaporator 52 becomes hydrogen peroxide vapor, which is a decontamination gas, as it is evaporated in the evaporator 52. A decontamination gas supply path 54 connected to a discharge side of the evaporator 52 is connected to the isolator compartment 4, the pass box 8, and the clean booth 10 via open-close valves 56, 58, 60, respectively. The open-close valves 56, 58, 60 configure a supply switcher that switches supply destinations of the decontamination gas.

A gas supply chamber 62 is arranged on a top side of the sterile operation area 2 and a branched path 54a of the decontamination gas supply path 54 is connected to the gas supply chamber 62. A HEPA filter 64 is arranged in the gas supply chamber 62, so that hydrogen peroxide gas supplied to the gas supply chamber 62 enters the sterile operation area 2 via the HEPA filter 64. Further, a gas supply chamber 66 is arranged on a top side of the pass box 8 as well and another branched path 54b of the decontamination gas supply path 54 is connected to the gas supply chamber 66. A HEPA filter 68 is arranged in the gas supply chamber 66 as well, so that hydrogen peroxide gas supplied to the gas supply chamber 66 enters the pass box 8 via the HEPA filter 68. Furthermore, the decontamination gas supply path 54 is connected to a gas supply chamber 70 that is arranged on a top side of the clean booth 10. Hydrogen peroxide vapor supplied to the gas supply chamber 70 enters the clean booth 10 via a HEPA filter 72 that is arranged in the gas supply chamber 70.

The clean gas supply unit 44 is connected to the isolator compartment 4, the pass box 8 (the outlet pass box 26), and the clean booth 10 (the air lock room 32). External air is blown by a fan 76 from a clean gas supply path 74 into the gas supply chamber 70, which is arranged on the top side of the clean booth 10, and enters the clean booth 10 via the HEPA filter 72 as being purified thereby. A catalyst 78 is arranged on an inlet side of the clean gas supply path 74 to prevent outflow of decontamination gas to the outside. Further, an open-close valve 80 is arranged on the upstream side of the fan 76 to block flow in that direction.

The inside of the clean booth 10 and the gas supply chamber of the isolator compartment 4 are connected by a gas introduction path 86, so that air in the clean booth 10 can be fed into the isolator compartment 4 by an intake blower 88 arranged in the gas introduction path 86. An air volume control valve 90 is arranged in the gas introduction path 86 so that the air volume fed to the isolator compartment 4 can be adjusted.

Further, external air can also be supplied to and discharged from the inside of the pass box 8 by the clean gas supply unit 44. An air supply fan 92 is arranged in the gas supply chamber 66, which is arranged in the top side of the pass box 8. With operation of the air supply fan 92, external air can be supplied from a gas supply path 94, which is connected to the gas supply chamber 66, into the pass box 8 via the HEPA filter 68. A gas discharge chamber 96 is arranged on a bottom side of the pass box 8 and a HEPA filter 98 is arranged in the gas discharge chamber 96 to prevent direct inflow of external air. A gas discharge path 100 is connected to the gas discharge chamber 96 so that the air supplied by the air supply fan 92 from the outside into the pass box 8 is discharged to the outside through the gas discharge path 100.

The clean gas supply path 94 and the gas discharge path 100 are provided with catalysts 102, 104, respectively. The catalyst 102 prevents outflow of decontamination gas. Further, in a case that air containing decontamination gas (hydrogen peroxide gas) in the pass box 8 is discharged outside through the air discharge path 100, the catalyst 104 decomposes and detoxifies the decontamination gas before it is discharged. Furthermore, open-close valves 106, 108 are arranged in the clean gas supply path 94 and the gas discharge path 100, respectively, to block flows through the respective paths 94, 100.

A discharge chamber 82 is provided with a HEPA filter 84 and a discharge path 110 is connected thereto. With operation of a discharge blower 112, air in the isolator compartment 4 can be discharged into the clean booth 10 through a catalyst 114. In a case that air containing decontamination gas (hydrogen peroxide vapor) in the isolator compartment 4 is discharged outside through the discharge path 110, the catalyst 114 decomposes and detoxifies the decontamination gas before it is discharged. An air volume control valve 116 is arranged in the discharge path 110 so that the volume of air to be discharged can be adjusted. A connection path 118 connects the discharge path 110 routed from the isolator compartment 4 with the air discharge path 100 routed from the pass box 8. An open-close valve 120 is arranged in the connection path 118 as well, so as to block flows through the connection path 118.

The connection path 118 connected to the air discharge path 100 of the pass box 8 and an induction side of the evaporator 52 are connected by a circulation path 122. With operation of a circulation blower 124 arranged in the circulation path 122, decontamination gas can be circulated. Pressure in the sterile operation area 2, the pass box 8 (the outlet pass box 26), and the clean booth 10 (the air lock room 32) is managed by controlling operation of the fans 76, 76, 92, the blowers 88, 112, which configure the clean gas supply unit 44, and adjusting the air volume control valves 90, 116.

In the following, a description of the operation of the isolator system 1 having the abovementioned structure will be provided. Before activation thereof, the system is decontaminated with decontamination gas (in the present embodiment, hydrogen peroxide vapor) supplied to the sterile operation area 2 in the isolator compartment 4, the pass box 8 (the outlet pass box 26), and the clean booth 10 (the air lock room 32) via the HEPA filters 64, 68, 72, which are arranged in the gas supply chambers 62, 66, 70, respectively.

In this case, the open-close valve 80 arranged in the clean gas supply path 74 of the clean gas supply unit 44, which supplies external air to the isolator compartment 4 and the clean booth 10, is closed; the open-close valve 106 arranged in the clean gas supply path 94 of the clean gas supply unit 44, which supplies air to the pass box 8, is closed; the open-close valve 108 arranged in the air discharge path 100 routed from the pass box 8 is closed; and the open-close valve 120 arranged in the connection path 118, which is connected to the air discharge path 100 routed from the pass box 8, is closed.

Then, the open-close valves 60, 56, 58 arranged in the decontamination gas supply path 54 and the branched paths 54a, 54b, which supply hydrogen peroxide gas from the evaporator 52 of the decontamination gas supply unit 42 to the clean booth 10, the isolator compartment 4, and the pass box 8, are opened, and further, the internal door 18 (the internal door 28) is opened to provide access via the opening portion 16a between the isolator compartment 4 and the pass box 8. Furthermore, the exit door 36 is opened to provide communication between the clean booth 10 and the air lock room 32.

In this state, the decontamination gas supply unit 42 is operated. That is, the pump 50 is driven to feed aqueous hydrogen peroxide from the tank 46 to the evaporator 52, and the circulation blower 124 arranged in the circulation path 122 and the intake blower 88 arranged in the gas introduction path 86, which is routed between the clean booth 10 and the isolator compartment 4, are driven. Accordingly, hydrogen peroxide vapor generated by evaporating the aqueous hydrogen peroxide in the evaporator 52 is supplied to the isolator compartment 4, the pass box 8, and the clean booth 10 through the decontamination gas supply path 54 and the branched paths 54a, 54b, via the HEPA filters 64, 68, 72, which are arranged in the gas supply chambers 62, 66, 70, respectively.

Hydrogen peroxide vapor after decontaminating the sterile operation area 2 inside of the isolator compartment 4, proceeds into the pass box 8 through the opening portion 16a located between the sterile operation area 2 and the pass box 8. Then, the hydrogen peroxide vapor flows back to the induction side of the evaporator 52 through the gas discharge path 100, the connection path 118, and the circulation path 122, along with the hydrogen peroxide vapor that decontaminated the inside of the pass box 8. Further, gas that decontaminated the inside of the clean booth 10 proceeds into the isolator compartment 4 through the gas introduction path 86 and is circulated via the pass box 8 along with the hydrogen peroxide vapor that decontaminated the inside of the isolator compartment 4.

Subsequently, the isolator compartment 4, the pass box 8, and the clean booth 10, which have already been decontaminated, are aerated, so that the decontamination gas is eliminated therefrom. At that time, all of the open-close valves 60, 56, 58 arranged in the decontamination gas supply path 54 and the branched paths 54a, 54b, which feed decontamination gas from the evaporator 52 of the decontamination gas supply unit 42 to the isolator compartment 4, the pass box 8, and the clean booth 10, are closed, while the internal door 18 between the isolator compartment 4 and the pass box 8 is kept opened. Further, the open-close valve 120 is opened. In this state, the fan 76 arranged in the gas supply chamber 70 of the clean booth 10 and the fan 92 arranged in the gas supply chamber 66 of the pass box 8 are driven. Further, the discharge blower 112 in the discharge path 110, which is routed from the isolator compartment 4, and the intake blower 88 in the gas introduction path 86, which is routed from the clean booth 10 to the isolator compartment 4, are driven.

According to the above, external air is taken into the gas supply chamber 70 of the clean booth 10 through the gas supply path 74 and proceeds into the clean booth 10 via the HEPA filter 72. Further, the air in the clean booth 10 travels through the gas introduction path 86 into the sterile operation area 2 in the isolator compartment 4 via the HEPA filter 64, which is arranged in the gas supply chamber 62 of the isolator compartment 4. Further, with operation of the fan 92 in the pass box 8, external air is taken into the gas supply chamber 66 through the gas supply path 94 and is introduced into the pass box 8 via the HEPA filter 68. Owing to the discharge blower 112, air in the isolator compartment 4 passing through the discharge path 110 and air in the pass box 8 passing through the discharge path 100 and the connection path 118 are joined together, and then are discharged into the clean booth 10 after a hydrogen peroxide component contained in the air is detoxified by the catalyst 114.

According to the abovementioned processes, decontamination and aeration after decontamination are carried out for the entire system including the isolator compartment 4, the pass box 8 (the outlet pass box 26), the clean booth 10, and the air lock room 32 of the isolator system 1. Subsequently, air pressure in the sterile operation area 2 is set to the highest positive pressure, air pressure in the pass box 8 is set to a positive pressure slightly lower than the pressure in the sterile operation area 2, and air pressures in the clean booth 10 and the air lock room 32 are set to a positive pressure lower than the pressure in the pass box 8, while all of the pressures are set to be equal to or higher than the ambient pressure in the building. Thus, a sterile state after decontamination is maintained.

Using the isolator system 1, the object 6 can be introduced and processed in the sterile operation area 2 in the isolator compartment 4. First, the object 6 to be processed in the sterile operation area 2 is placed into the pass box 8. Here, the internal door 18 between the isolator compartment 4 and the pass box 8 is closed (being in a state illustrated in FIG. 3) to block communication between the isolator compartment 4 and the pass box 8, and then the external door 22 is opened and the object 6 is inserted. Subsequently, the external door 22 is closed and the pass box 8 is hermetically sealed.

Next, the object 6 in the pass box 8 is decontaminated. Here, the open-close valve 60 arranged in the decontamination gas supply path 54 routed from the evaporator 52 of the decontamination gas supply unit 42 to the clean booth 10 is closed, the open-close valve 56 arranged in the branched path 54a routed to the isolator compartment 4 is closed, and the open-close valve 58 arranged in the branched path 54b routed to the pass box 8 is opened. Further, the open-close valve 120 arranged in the connection path 118 and the open-close valve 108 arranged in the discharge path 100 are closed. In this state, the pump 50 of the decontamination gas supply unit 42 is driven to feed aqueous hydrogen peroxide to the evaporator 52, and then hydrogen peroxide vapor produced in the evaporator 52 is supplied selectively into the pass box 8. After the object 6 is decontaminated by the hydrogen peroxide vapor in the pass box 8, the hydrogen peroxide vapor is circulated by the circulation blower 124 and flows back to the induction side of the evaporator 52 through the HEPA filter 98 in the discharge chamber 96, via the discharge path 100, the connection path 118, and the circulation path 122.

After the object 6 to be processed in the sterile operation area 2 is decontaminated in the pass box 8, aeration is carried out. In this process, the circulation blower 124 is stopped, the open-close valves 60, 56, 58 arranged in the decontamination gas supply path 54 and the branched paths 54a, 54b of the decontamination gas supply unit 42 are closed, the open-close valve 106 arranged in the gas supply path 94 of the clean gas supply unit 44 is opened, and the open-close valve 108 arranged in the discharge path 100 is opened. With operation of the fan 92 arranged in the gas supply chamber 66, clean gas supplied into the pass box 8 through the clean gas supply path 94 and the HEPA filter 68 passes through the HEPA filter 98, which is arranged in the gas discharge chamber 96, and is discharged outside through an outlet side opening portion of the discharge path 100 after hydrogen peroxide is detoxified by the catalyst 104.

After the aeration is performed, the internal door 18 is opened, and then the object 6 decontaminated in the pass box 8 is introduced into the sterile operation area 2 in the isolator compartment 4. Then, the object 6 can be processed in a state inside of the isolator compartment 4 that is hermetically sealed with the internal door 18 closed. The processed object 6 is then transferred to the outlet pass box 26. After decontamination is performed, similarly to that performed in the pass box 8 at the time of insertion, to eliminate risk of contamination due to viruses or the like, the processed object 6 can be removed to the clean booth 10. In a case of subsequently treating cells derived from another donor, decontamination gas is supplied to the sterile operation area 2 selectively while the open-close valve 56 is opened and the open-close valves 58, 60 are closed so that the pass box 8 and the clean booth 10 are not decontaminated; only the sterile operation area 2 is decontaminated.

In the present embodiment, the system is configured with an outlet pass box 26 so that the object 6 is moved in one direction. However, as illustrated in FIG. 1, it is also possible to adopt a structure in which the pass box 8 functions as an inlet-outlet pass box, thereby eliminating the outlet pass box 26 and decontaminating the processed object 6 in the pass box 8.

As described above, in the isolator system 1 according to the present embodiment, decontamination occurs when decontamination gas is supplied into the isolator compartment 4 by the decontamination gas supply unit 42 and the inside thereof is maintained at a positive pressure by the clean gas supply unit 44. Accordingly, the sterile operation area 2 arranged in the isolator compartment 4 can be maintained in a sterile condition. In addition, the pass box 8, which is arranged for insertion and removal of the object 6 to and from the sterile operation area 2, can be maintained in a highly sterilized state.

Accordingly, even if an ambient environment of the isolator compartment 4, in which the sterile operation area 2 is arranged, is the basic structure of the clean booth 10 with relatively low grade D cleanliness, the sterile operation area 2 can be approved as grade A with the highest cleanliness. Therefore, it is possible to use the sterile operation area 2 as an important operation region for conducting research on human cells and tissue cultures. Further, decontamination gas can be supplied to the grade D clean booth 10 by the decontamination gas supply unit 42. Therefore, it is possible to easily maintain cleanliness at a predetermined level or higher while preventing contamination by decontaminating the clean booth 10 at regular intervals.

In the first embodiment, the sterile operation area 2 is arranged in the isolator compartment 4 and a decontamination function is provided for a pass box (the inlet pass box 8 and the outlet pass box 26) through which the object 6 is moved to and from the sterile operation area 2. Accordingly, the sterile operation area 2 enclosed by the grade D clean booth 2 can be used as a grade A clean room. In contrast, a second embodiment provides an isolator system 201 with a sterile operation area 202 arranged in an isolator compartment 204 to have an environment of grade A even if a decontamination function is not provided for a pass box by dividing the pass box into a plurality of steps.

In the second embodiment, a clean booth 210 with an environment of grade D similar to the clean booth 10 of the first embodiment is provided. The clean booth 210 encloses an external insertion port 214a of a glove 214 arranged in the isolator compartment 204 in which the sterile operation area 202 is arranged, external insertion ports of a later-mentioned pass box and another room, and an inlet port and an outlet port of an object. Further, a plurality of pass boxes without decontamination capabilities are connected together for transferring an object 206 into the sterile operation area 202 of the isolator compartment 204. An inlet pass box 208 is configured at one end of the plurality of pass boxes. An internal door 218 through which the object 206 in the inlet pass box 208 is transported into the isolator compartment 204 is arranged at a wall face 216 of the isolator compartment 204, which is connected to the inlet pass box 208.

An entrance door 220 through which an operator 212 can enter and exit is arranged at an entrance side of the clean booth 210. In addition to the isolator compartment 204 and the inlet pass box 208, the plurality of pass boxes are arranged in the clean booth 210. An entrance pass box 222 is arranged at a position that is closest to the entrance door 220 and farthest from the inlet pass box 208. The entrance pass box 222 does not have a decontamination function and therefore has a grade D cleanliness environment, the same as that in the clean booth 210. An open-close door 224, through which the object 206 to be processed in the sterile operation area 202 can be placed by the operator 212 in the clean booth 210, is arranged at the entrance pass box 222.

A dust removal pass box 228 is connected to one side wall 226 of the entrance pass box 222. A sterile air nozzle 230 that blows air to remove dust from the object 206 placed inside is arranged in the dust removal pass box 228. A wearing entity (i.e., a glove 234) is arranged in a side wall 232 of the dust removal pass box 228 facing the clean booth 210, enabling the operator 212 in the clean booth 210 to process the object 206 in the dust removal pass box 228. An open-close door 236 through which the object 206 can be inserted and removed is arranged at a side wall 226 between the entrance pass box 222 and the dust removal pass box 228.

Another pass box (hereinafter, called a relay pass box 240) without a decontamination capabilities is connected to a side wall 238 of the dust removal pass box 228 opposite from the side wall 226 which is connected to the entrance pass box 222. The relay pass box 240 is for transferring the object 206, from which dust has been removed by sterilized air blowing from the sterile air nozzle 230, from the dust removal pass box 228 to a sterilization pass box 242. An open-close door 244 is arranged in the side wall 238 between the relay pass box 240 and the dust removal pass box 228.

The sterilization pass box 242 is connected to a side wall 246 of the relay pass box 240 that is different from the side wall 238 connected to the dust removal pass box 228. The sterilization pass box 242 is provided with an alcohol injection nozzle 248 as a sterilizer to sterilize the object 206 stored therein. A wearing entity (i.e., a glove 252) is arranged in a side wall 250 of the sterilization pass box 242 facing the clean booth 210, enabling the operator 212 in the clean booth 210 to process the object 206 in the sterilization pass box 242. An open-close door 254 through which the object 206 can be inserted and removed is arranged in a side wall 246 between the relay pass box 240 and the sterilization pass box 242. The inlet pass box 208 is connected to a side wall 256 of the sterilization pass box 242 opposite from the side wall 246 which is connected to the relay pass box 240. An open-close door 258 which provides access between the sterilization pass box 242 and the inlet pass box 208 is arranged in the side wall 256. The inlet pass box 208 also does not have decontamination capabilities.

An incubator 260 is connected to a side wall 259 (a wall on an exit side of the isolator compartment 204) of the isolator compartment 204 opposite from the side wall 216 to which the inlet pass box 208 is connected. An open-close door 262 through which the object 206 is removed from the inside of the isolator compartment 204 is arranged in the side wall 259. In the present embodiment, the decontamination gas supply unit 42, which is similar to that in the first embodiment, is connected to the sterile operation area 202 arranged in the isolator compartment 204 and the clean booth 210. However, the inlet pass box 208 through which the object 206 is moved into the sterile operation area 202 is not connected to the decontamination gas supply unit 42 and the object 206 cannot be decontaminated in the inlet pass box 208, which is configured only to pass the object 206 directly from the preceding sterilization pass box 242.

In the second embodiment, the inside of the clean booth 210 of the isolator system 201, which is installed in a room in a building, is decontaminated by the decontamination gas supply unit 42 and the air pressure inside the clean booth 210 is maintained at a positive pressure equal to or higher than the ambient air pressure in the building by the clean gas supply unit 44. Accordingly, a grade D cleanliness environment is provided similar to the first embodiment. Further, the interiors of the sterile operation area 202, the incubator 260, the inlet pass box 208, the sterilization pass box 242, the relay pass box 240, the dust removal pass box 228, and the entrance pass box 222 are to be decontaminated with decontamination gas that is supplied to the sterile operation area 202 by the decontamination gas supply unit 242 in a state that the respective open-close doors 262, 218, 258, 254, 244, and 236 are opened. Further, owing to that the respective insides are maintained at positive pressures by the clean gas supply unit 44, sterility can be ensured.

In this case, the highest pressure is set in the sterile operation area 202 and the incubator 260. Then, the pressure gradually decreases from the inlet pass box 208 to the entrance pass box 222 to produce a pressure difference. Since the entrance pass box 222 adjoins the clean booth 210, the pressure therein is approximately equal to that in the clean booth 210. According to the abovementioned structure, it is possible that, based on the clean booth 210 being grade D, the dust removal pass box 228 is set to be grade C while the cleanliness the entrance pass box 222 is arranged between the clean booth 210 and the dust removal pass box 228, the sterilization pass box 242 is set to be grade B while the relay pass box 240 is arranged between the dust removal pass box 228 and the sterilization pass box 242, and further, the sterile operation area 202 and the inside of the incubator 260 is set to be grade A while the cleanliness of the inlet pass box 208 is arranged between the sterilization pass box 242 and the sterile operation area 202.

In the isolator system 201 having the abovementioned structure, the object 206 (for example, a culture vessel for human cells) transported through the entrance door 220 of the clean booth 210 is first introduced into the entrance pass box 222. Since the entrance pass box 222 is arranged as an air lock room, the object 206 passed directly through the entrance pass box 222 and is placed into the dust removal pass box 228. The dust removal pass box 228 is provided with the sterile air nozzle 230 as a dust remover, so that the inside environment thereof is set at a level of grade C. The object 206, with dust removed in the dust removal pass box 228, is transported into the next relay pass box 240. Since the relay pass box 240 is arranged as an air lock room as well, the object 206 passes directly through the relay pass box 240 and is introduced into the next sterilization pass box 242.

The sterilization pass box 242 is provided with the alcohol injection nozzle 248 as a sterilizer, so that the inside environment thereof is set at a level of grade B. The object 206, on which a sterilization process has been performed in the sterilization pass box 242, is introduced into the next inlet pass box 208. Since the inlet pass box 208 is arranged as an air lock room as well, the object 206, on which the sterilization process has been performed in the grade B environment is moved directly into the sterile operation area 202 in the isolator compartment 204 and is processed therein.

After processing, a culture of human cells is performed in the incubator 260 for a predetermined period of time. When the culture for the predetermined period of time is completed, the object 206 is brought out into the sterile operation area 202, and then, an outer surface thereof is sterilized in the sterilization pass box 242 after passing through the inlet pass box 208. Subsequently, the object 206 is brought out into the clean booth 210 after passing through the relay pass box 240, the dust removal pass box 228, and the entrance pass box 222. In a case of subsequently treating cells derived from another donor, decontamination gas is selectively supplied to the sterile operation area 202 by the decontamination gas supply unit 42, so that the sterile operation area 202, the incubator 260, and respective pass boxes from the inlet pass box 208 to the entrance pass box 222 are decontaminated.

The isolator system 201 according to the second embodiment is not provided with a pass box with a decontamination capabilities for the object 206 brought into the sterile operation area 202, which is arranged in the isolator compartment 204. Here, in order to enhance cleanliness stepwise, each of the entrance pass box 222, the relay pass box 240, and the inlet pass box 208 is arranged as an intermediate air lock room and the dust removal pass box 228 and the sterile pass box 242 are arranged as grade C and grade B environment, respectively. In each pass box, when one door is opened, the other door is closed to prevent direct communication between environments of different grades. According to the above, the object 206 can sequentially pass through intermediate air lock rooms while performing open-close operation of the respective open-close doors 224, 236, 244, 254, 258, 218. As a result, research and processing can be carried out on cultures of human cells and tissues, and the like in a grade A cleanliness environment of the sterile operation area 202 and the incubator 260.

In each of the abovementioned embodiments, the clean booth 10, 210 is installed in a room in a building. However, it is also possible to configure the isolator system 1, 201 of the present invention with the isolator compartment 4, 204 arranged in a room in a building as regarding the room as a clean booth. In this case, the gas supply chamber 70 and the HEPA filter 72 are configured in the isolator compartment 4, 204 and clean gas and the decontamination gas are blown into the room from a side wall thereof. According to such a structure, the isolator system 1, 201 can be easily arranged by simply installing the isolator compartment 4, 204 in any room without modifying the building and its interior. Further, in the isolator system 1 of the first embodiment, it is also possible to arrange the incubator 260 inside of the isolator compartment 4.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2013-073950 (filed on Mar. 29, 2014) which is expressly incorporated herein, by reference, in its entirety.

The invention claimed is:

1. An isolator system, comprising:
   an isolator in which a sterile operation area is provided and which includes a wearing entity for an operator to operate externally;
   a pass box for transferring an object into the sterile operation area;
   a clean booth into which an operator can enter, which encloses at least an external insertion port of the wearing entity of the isolator and an object inlet port for inserting the object into the pass box,
   a clean gas supply that supplies clean air to an interior of the clean booth and, from the clean booth to the sterile operation area; and
   a decontamination gas supply that includes a plurality of switches that selectively supply decontamination gas into the sterile operation area, the clean booth and the pass box,
   the isolator, the pass box, and the clean booth being arranged in a building, and
   after an interior of the sterile operation area and the clean booth are decontaminated with the decontamination gas to achieve a decontaminated condition, by the decontamination gas supply, interior pressures of the sterile operation area and of the clean booth are maintained equal to or higher than an environmental pressure in the building, by the clean gas supply to maintain the decontaminated condition and the interior pressure of the clean booth is maintained lower than the interior pressure of the sterile operation area.

2. The isolator system according to claim 1, further comprising an air lock room between the clean booth and an ambient environment, wherein an interior air pressure of the air lock room is maintained higher than an ambient pressure in the building.

3. The isolator system according to claim 1, wherein the pass box is divided into a plurality of sections.

4. The isolator system according to claim 1, the pass box comprising a first pass box, the system further comprising a second pass box having an outlet port for transferring an object out of the sterile operation area, the second pass box being provided opposite the first pass box with respect to the sterile operation area, the clean booth enclosing the outlet port.

5. The isolation system according to claim 1, further comprising a dust removal pass box and a sterilization pass box that are configured to receive an object and to convey the object to the sterile operation area.

\* \* \* \* \*